United States Patent [19]
Patoiseau et al.

[11] Patent Number: 5,990,173
[45] Date of Patent: Nov. 23, 1999

[54] 2,3,5-TRIMETHYL-4-HYDROXYANILIDE DERIVATIVES, PREPARATION THEREOF AND THERAPEUTICAL USE THEREOF

[75] Inventors: Jean-François Patoiseau, Castres; Jean-Marie Autin, Labruguiere; André Delhon; Philippe Oms, both of Castres; Didier Junquero, Burlats, all of France

[73] Assignee: Pierre Fabre Medicament, Boulogne, France

[21] Appl. No.: 09/077,420

[22] PCT Filed: Nov. 27, 1996

[86] PCT No.: PCT/FR96/01877

§ 371 Date: May 27, 1998

§ 102(e) Date: May 27, 1998

[87] PCT Pub. No.: WO97/19918

PCT Pub. Date: Jun. 5, 1997

[30] Foreign Application Priority Data

Nov. 28, 1995 [FR] France ................... 95 14086

[51] Int. Cl.⁶ .......................... A61K 31/16; C07C 233/05
[52] U.S. Cl. .................. 514/625; 514/618; 514/629; 514/824; 564/162; 564/215; 564/223
[58] Field of Search ................... 514/618, 625, 514/629, 824; 564/162, 215, 223

[56] References Cited

U.S. PATENT DOCUMENTS 5,254,590 10/1993 Malen et al. ................... 514/613

FOREIGN PATENT DOCUMENTS 0 559 898 9/1993 European Pat. Off.
0 619 312 10/1994 European Pat. Off.

OTHER PUBLICATIONS

M Sato et al, Patent Abstracts of Japan 18(262) May 19, 1994.

*Primary Examiner*—Shailendra Kumar
*Attorney, Agent, or Firm*—The Firm of Gordon W. Hueschen

[57] ABSTRACT

Novel 2,3,5-trimethyl-4-hydroxyanilide derivatives of general formula I, wherein, e.g., $R_1$ is phenyl, $R_2$ is H, $R_3$ is $C_{12}H_{25}$, and A is a sulphur atom, are disclosed. A method for preparing said derivatives, pharmaceutical compositions containing at least one of said compounds as active principle, and the use of such derivatives for treating hypercholesterolemia or atherosclerosis.

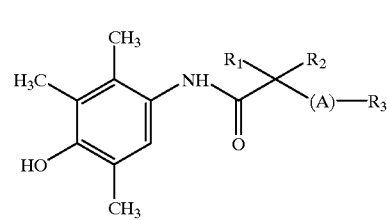

(I)

12 Claims, No Drawings

2,3,5-TRIMETHYL-4-HYDROXYANILIDE DERIVATIVES, PREPARATION THEREOF AND THERAPEUTICAL USE THEREOF

The present application is a U.S. National Application filed under 35 USC 371 of PCT/FR96/01877, filed Nov. 27, 1996 based upon French application Ser. No. 95/14086 filed Nov. 28, 1995.

The subject-matter of the present invention is novel anilide derivatives, their preparation and their application in human therapeutics.

It also relates to the use of these derivatives in the manufacture of medicaments intended for the treatment of hypercholesterolemia or of atherosclerosis.

Dietary cholesterol is absorbed in the form of free cholesterol by intestinal cells and then esterified by the enzyme ACAT (acyl-CoA: cholesterol O-acyltransferase) in the serum. Inhibition of ACAT prevents the intestinal absorption and the accumulation of cholesterol in arterial tissue. In addition, low density lipoproteins (LDL) are, after oxidation, captured by scavenger receptors and result in the formation of the foam cell, the site of initiation of the atheromatous plaque (D. Steinberg et al., England. J. Med., 320, 915–924, 1989).

The object of the present invention is targeted at obtaining novel hypocholesterolemic and antioxidant derivatives which can act both on the amount and the quality of the LDL, with the aim of reducing their atherogenic potential and their long-term deleterious effects on the vascular wall.

The compounds of the present invention correspond to the general formula I

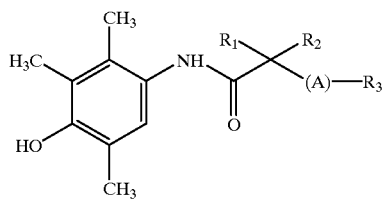

in which:

$R_1$ and $R_2$, which are identical or different, represent, independently of one another:
- hydrogen
- a linear or branched $C_1$–$C_6$ alkyl radical
- an aromatic group, such as phenyl, naphthyl or pyridyl, optionally substituted by one or more $C_1$–$C_4$ alkyl, $C_1$–$C_4$ alkoxy, hydroxyl or halo groups R3 represents a linear or branched $C_6$–$C_{15}$ alkyl chain or a phenyl group optionally substituted by one or more $C_1$–$C_4$ alkyl, $C_1$–$C_4$ alkoxy, hydroxyl or halo groups A represents an oxygen or sulfur atom or the sulfoxy group.

As it is possible for the compounds of general formula I to possess asymmetric centers, the present invention covers the various stereoisomers or enantiomers and their mixtures.

The compounds of general formula I can be used in the preparation of pharmaceutical compositions or of medicaments intended for the treatment of diseases such as hypercholesterolemia or atherosclerosis.

Finally, the synthetic processes which make it possible to access the compounds of general formula I also form part of the present invention.

The compounds of general formula I can be obtained according to one of the following methods (Scheme I):

Method A:
a) Treatment of 2,3,6-trimethyl-4-aminophenol hydrochloride with an α-haloacyl halide II, in which Hal and Hal' represent bromine or chlorine and $R_1$ and $R_2$ have the same meaning as above, in the presence of a base, such as triethylamine, in order to access the compound III.

b) Treatment of the compound III with the derivative IV, in which $R_3$ and A have the same meaning as above, in a sodium/methanol or potassium tert-butoxide/tert-butanol medium, in order to give the compound I.

Method B:

Treatment of 2,3,6-trimethyl-4-aminophenol hydrochloride with an α-halo acid V, in which Hal, $R_1$ and $R_2$ have the same meaning as above, in the presence of an activator, such as dicyclohexylcarbodiimide or 2-chloro-1-methylpyridinium iodide, and of a base, such as triethylamine, in order to access the compound III, subsequently treated in a way identical to that described in Method A-b.

Method C:

Treatment of 2,3,6-trimethyl-4-aminophenol hydrochloride with the derivative IV, in which $R_1$, $R_2$, $R_3$ and A have the same meaning as above, in the presence of an activator, such as dicyclohexylcarbodiimide or 2-chloro-1-methylpyridinium iodide, and of triethylamine, in order to give the compound I.

SCHEME I

METHOD A

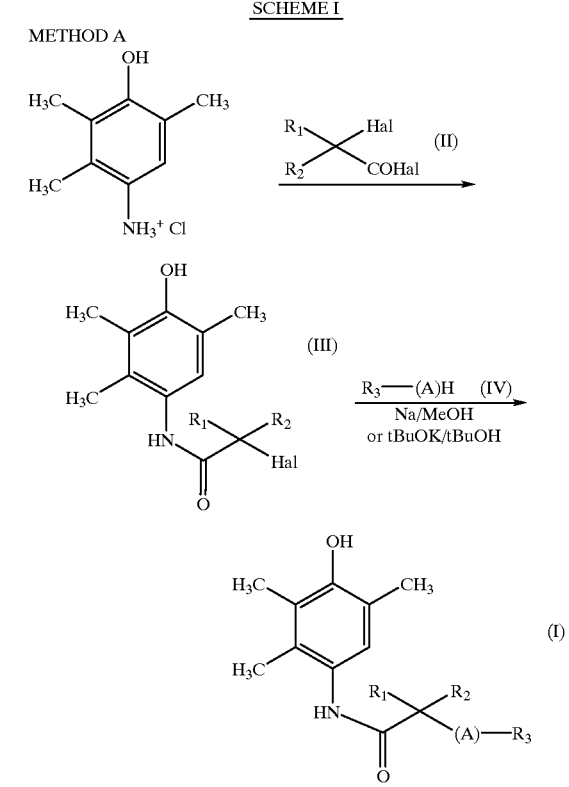

METHOD B

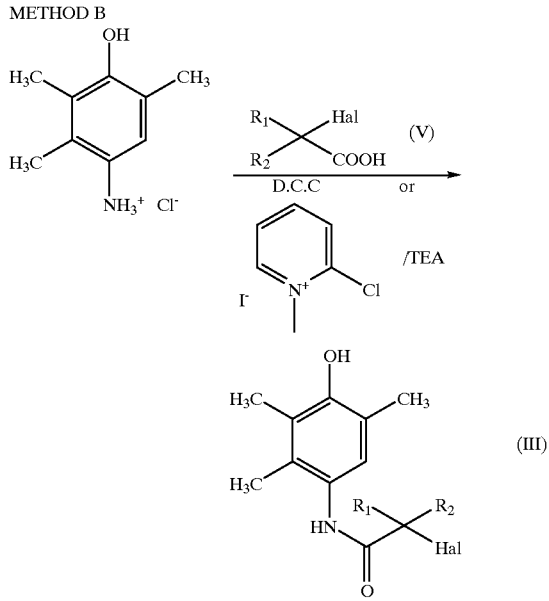

METHOD C

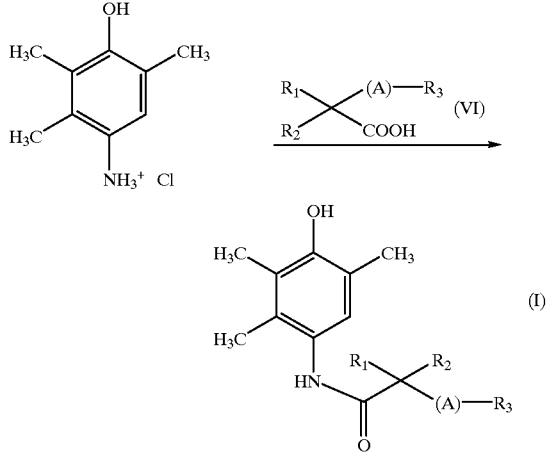

The invention can be better understood using the following non-limiting examples which constitute advantageous embodiments according to the invention.

EXAMPLE 1
(Method A) 2',3',5'-Trimethyl-4'-hydroxy-α-(dodecylthio) propionanilide 1.

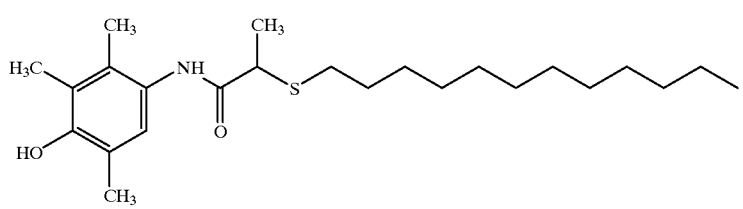

a—2',3',5'-Trimethyl-4'-hydroxy-α-bromopropionanilide 1a.

Triethylamine (3.48 ml; 0.25 mol) is added to a solution of 2,3,6-trimethyl-4-aminophenol hydrochloride (1.87 g; 0.01 mol) in dimethylformamide placed under nitrogen. α-Bromopropionyl chloride (1.32 ml; 0.0125 mol) is subsequently added dropwise and the reaction mixture is stirred for one hour at room temperature.

After diluting with water, extraction is carried out with ethyl acetate. The organic phase is washed with N hydrochloric acid and with water and then dried ($MgSO_4$) and concentrated to dryness under vacuum. The residue is taken up in hexane, filtered off and dried to give the compound 1a (2.10 g).

M.p.=186° C. TLC: silica gel 60F254 Merck Rf=0.61 (AcOEt).

b—2',3',5'-Trimethyl-4'-hydroxy-α-(dodecylthio) propionanilide 1.

n-Dodecanethiol (2.11 ml; 0.0088 mol) is dissolved in methanol (20 ml) and then sodium methoxide (0.47 g; 0.0088 mol) is added. After a contact time of 15 minutes, the compound 1a (2.10 g; 0.0073 mol) is added and the reaction mass is brought to 60° C. for 2 hours. The methanol is subsequently evaporated off and then the residue is extracted with ethyl acetate.

The organic phase, washed with water and then dried ($MgSO_4$), is concentrated to dryness under vacuum. The residue obtained is purified by flash chromatography (elution: 30/70 ethyl acetate/hexane) to give 1.24 g of white crystals (1).

M.p.=123° C. TLC: silica gel 60F254 Merck Rf=0.59 (50/50 AcOEt/hexane).

EXAMPLE 2

2',3',5'-Trimethyl-4'-hydroxy-α-(dodecylthio)acetanilide 2.

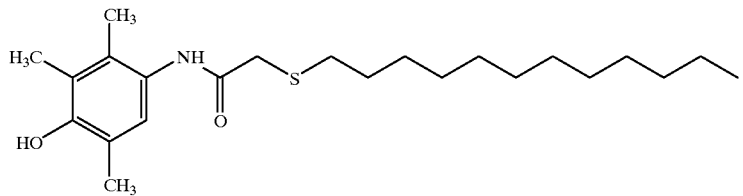

This compound is prepared according to the process described in Example 1, by using bromoacetyl bromide.

M.p.=99° C. TLC: silica gel 60F254 Merck Rf=0.51 (50/50 AcOEt/hexane).

EXAMPLE 3

2',3',5'-Trimethyl-4'-hydroxy-α-(dodecylthio)butyranilide 3.

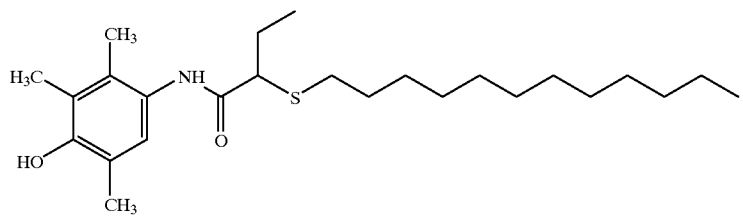

This compound is prepared according to the process described in Example 1, by using 2-bromobutyryl bromide.

M.p.=127° C. TLC: silica gel 60F254 Merck Rf=0.61 (50/50 AcOEt/hexane).

EXAMPLE 4

2',3',5'-Trimethyl-4'-hydroxy-α-(dodecylthio)hexananilide 4.

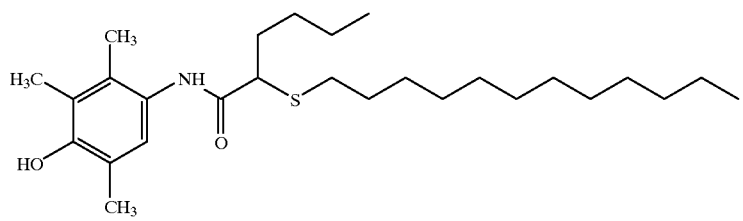

This compound is prepared according to the process described in Example 1, by using 2-bromohexanoyl bromide.

EXAMPLE 5

2',3',5'-Trimethyl-4'-hydroxy-α-(dodecylthio)isovaleranilide 5.

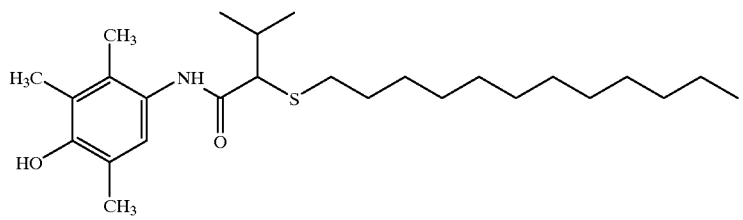

M.p.=80° C. TLC: silica gel 60F254 Merck Rf 0.36 (30/70 AcOEt/hexane).

This compound is prepared according to the process described in Example 1, by using 2-bromoisovaleryl chloride.

M.p.=123° C. TLC: silica gel 60F254 Merck Rf=0.30 (30/70 AcOEt/hexane).

EXAMPLE 6

2',3',5'-Trimethyl-4'-hydroxy-α-(dodecylthio)valeranilide 6.

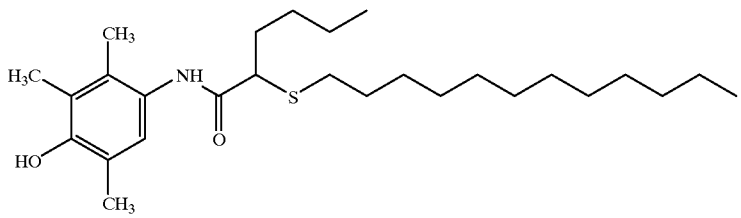

This compound is prepared according to the process described in Example 1, by using 2-bromovaleryl bromide. M.p.=116° C. TLC: silica gel 60F254 Merck Rf=0.39 (30/70 AcOEt/hexane).

EXAMPLE 7

(Method B) 2',3',5'-Trimethyl-4'-hydroxy-α-dodecylthio-α-phenylacetanilide 7.

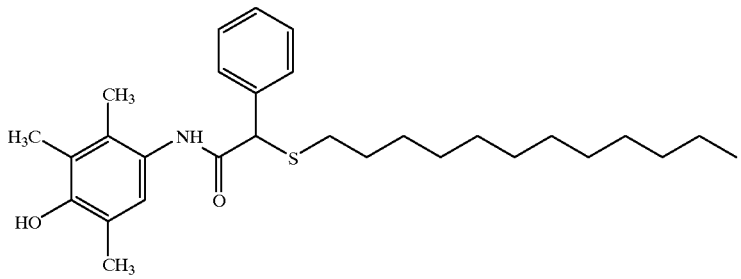

a)—2',3',5'-Trimethyl-4'-hydroxy-α-chloro-α-phenylacetanilide 7a.

Triethylamine (0.94 ml; 0.0067 mol) is added to a suspension of 2,3,6-trimethyl-4-aminophenol hydrochloride (1.27 g; 0.0067 mol) in methylene chloride (35 ml) placed under nitrogen.

α-Chlorophenylacetic acid (1.27 g; 0.0074 mol) and dicyclohexylcarbodiimide (1.54 g; 0.0074 mol) are subsequently added and the reaction mixture is vigorously stirred for 2 hours at room temperature.

After filtering off the dicyclohexylurea formed, the organic phase is washed with N/10 hydrochloric acid, with water and then with aqueous saline solution. After drying (MgSO$_4$) and evaporating to dryness under vacuum, the residue is taken up in ethyl ether. The crystals formed are filtered off and dried to give the compound 7a (1.22 g).

M.p.=199° C. TLC: silica gel 60F254 Merck Rf=0.68 (50/50 AcOEt/hexane).

b)—2',3',5'-Trimethyl-4'-hydroxy-α-dodecylthio-α-phenylacetanilide 7.

The compound is prepared according to the technique described in Example 1b, starting from the compound 7a.

M.p.=129° C. TLC: silica gel 60F254 Merck Rf=0.64 (50/50 AcOEt/hexane).

EXAMPLE 8

(Method C) 2',3',5'-Trimethyl-4'-hydroxy-α-(dodecylthio)isobutyranilide 8.

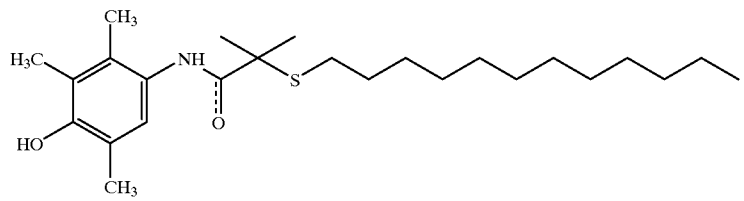

2,3,6-Trimethyl-4-aminophenol hydrochloride (3.52 g; 0.018 mol), α-(dodecylthio)isobutyric acid (5.41 g; 0.018 mol) and triethylamine (9.4 ml; 0.067 mol) are successively added to a suspension of 2-chloro-1-methylpyridinium iodide (5.75 g; 0.022 mol) in chloroform (225 ml) and then the reaction mixture is heated at reflux for 2 hours. The reaction mass is cooled, diluted with ethyl ether (350 ml) and then filtered. This organic phase is subsequently washed with N hydrochloric acid, with water and then with aqueous saline solution. After drying (MgSO$_4$) and concentrating to dryness under vacuum, the residue is taken up in isopropyl ether and filtered off to give 7.32 g of white crystals of the compound 8.

M.p.=71° C. TLC: silica gel 60F254 Merck Rf=0.65 (50/50 AcOEt/hexane).

EXAMPLE 9

2',3',5'-Trimethyl-4'-hydroxy-α-(p-chlorophenylthio) isobutyranilide 9.

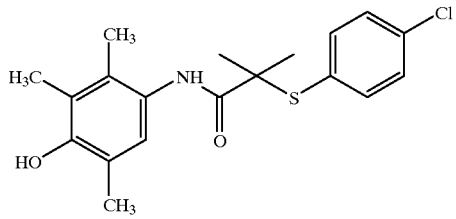

This compound is prepared according to the process described in Example 8, by using α-(p-chlorophenylthio) isobutiric acid.

M.p.=134° C. TLC: silica gel 60F254 Merck Rf=0.54 (50/50 AcOEt/hexane).

EXAMPLE 10

2',3',5'-Trimethyl-4'-hydroxy-α-(p-chlorophenylsulfinyl) isobutyranilide 10.

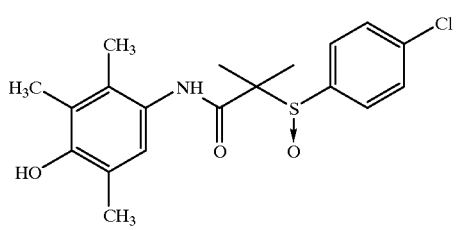

This compound is prepared according to the process described in Example 8, by using α-(p-chlorophenylsulfinyl)isobutyric acid.

M.p.=157–158° C. TLC: silica gel 60F254 Merck Rf=0.33 (50/50 AcOEt/hexane).

EXAMPLE 11

2',3',5'-Trimethyl-4'-hydroxy-α-(p-chlorophenoxy) isobutyranilide.

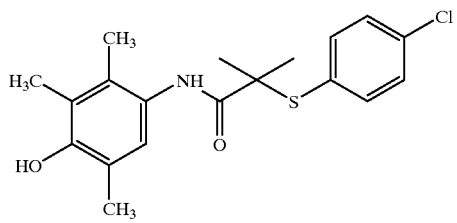

Ethyl chloroformate (0.96 ml; 0.01 mol) is added dropwise to a solution, cooled to 0° C., of clofibric acid (2.14 g; 0.01 mol) and of triethylamine (1.48 ml; 0.0105 mol) in tetrahydrofuran (25 ml). After stirring for 20 minutes, the mixed anhydride obtained is added slowly to a suspension of 2,3,6-trimethyl-4-aminophenol hydrochloride (1.87 g; 0.01 mol) in dimethylformamide (10 ml) and triethylamine (1.48 ml; 0.0105 mol).

The reaction mixture, kept under a nitrogen stream, is stirred for 1 hour at 5° C. and then for 12 hours at room temperature, then poured into water and extracted with ethyl acetate. The organic phase is washed with water and with aqueous saline solution, dried over MgSO$_4$ and then evaporated to dryness under vacuum. The residue is crystallized from ethyl ether and then recrystallized from ethyl acetate to give the compound 11.

M.p.=175° C. TLC: silica gel 60F254 Merck Rf=0.30 (30/70 AcOEt/hexane).

EXAMPLE 12

2',3',5'-Trimethyl-4'-hydroxy-α-(dodecylsulfinyl) bobutyranilide 12.

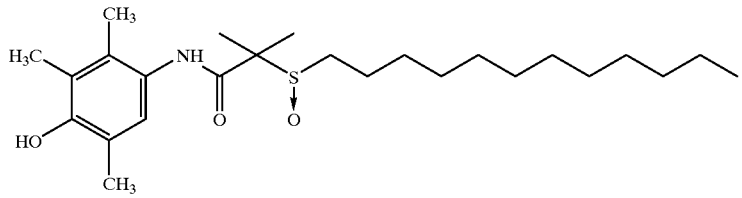

This compound is prepared according to the process described in Example 8, by using α-(dodecylsulfinyl) isobutyric acid.

M.p.=73° C. TLC: silica gel 60F254 Merck Rf=0.43 (AcOEt/hexane).

EXAMPLE 13
2',3',5'-Trimethyl-4'-hydroxy-α-dodecylthio-α-3,5-di-tert-butyl-4-hydroxyphenylacetanilide 13.

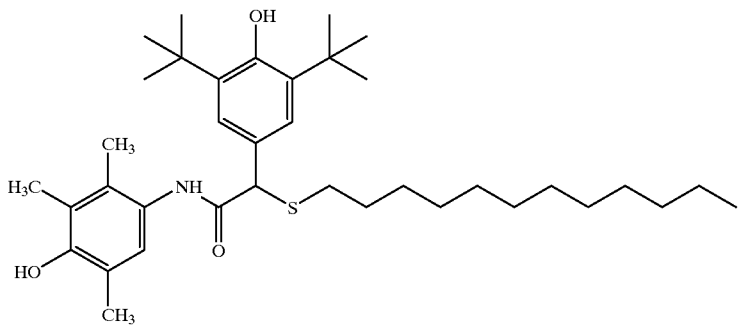

This compound is prepared according to the method described in Example 11, by using α-dodecylthio-3,5-di-tert-butyl-4-hydroxyphenylacetic acid.
M.p.=150° C. TLC: silica gel 60F254 Merck Rf=0.31 (30/70 AcOEt/hexane).

EXAMPLE 14
2',3',5'-Trimethyl-4-hydroxy-α-dodecylthio-α-(p-methoxyphenyl)acetanilide 14.

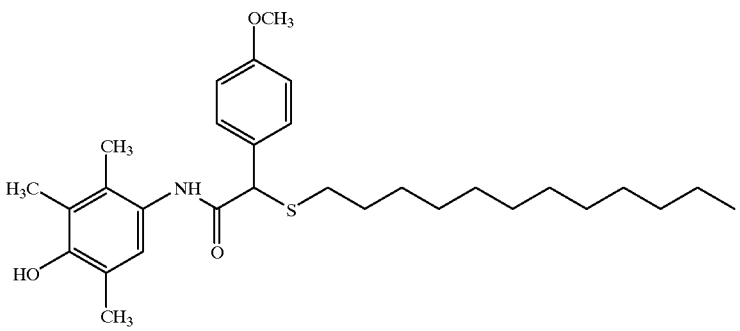

This compound is prepared according to the method described in Example 7a, by using α-dodecylthio-α-(p-methoxyphenyl)acetic acid.

M.P.=122° C. TLC: silica gel 60F254 Merck Rf=0.74 (30/70 AcOEt/hexane).

EXAMPLE 15
2',3',5'-Trimethyl-4'-hydroxy-α-dodecylthio-α-naphthylacetanilide 15.

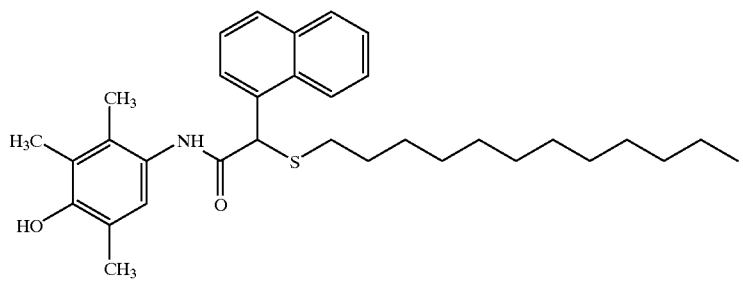

This compound is prepared according to the method described in Example 7a, by using α-dodecylthio-α-naphthylacetic acid.

M.p.=134° C. TLC: silica gel 60F254 Merck Rf: 0.60 (95/5 $CH_2Cl_2$/AcOEt).

EXAMPLE 16

(+)-2',3',5'-Trimethyl-4'-hydroxy-α-dodecylthio-α-phenylacetanilide 16.

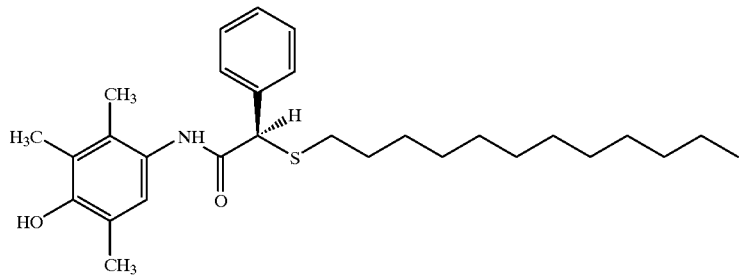

This compound is prepared according to the method described in Example 7a, by using (+)-α-dodecylthio-α-phenylacetic acid.

M.p.=128° C. TLC: silica gel 60F254 Merck Rf=0.64 (50/50 AcOEt/hexane). $\alpha_D^{25}$=+34.7° (C=0.5; ethanol).

The compounds of the invention were subjected to pharmacological tests which showed their potential value in the treatment of hypercholesterolemia and in the treatment of atheromatous disease.

The compounds were studied for their inhibitory effect on ACAT and hypocholesterolemic effect in rats, on the one hand, and for their antioxidant effect, on the other hand.

1) Inhibition of ACAT

The inhibitory activity of the compounds with respect to ACAT (acyl-CoA:cholesterol O-acyl-transferase enzyme) was evaluated in vitro using the technique of H. Chautan et al. (Analytical Biochemistry, 173, 436–439, 1988).

The activities, expressed as 50% inhibitory concentrations ($IC_{50}$), obtained with some products of the invention are recorded, by way of example, in Table 1 below:

TABLE 1

| Compounds No. | $IC_{50}$ (μM) |
|---|---|
| 2 | 0.30 |
| 3 | 0.31 |
| 4 | 0.16 |
| 5 | 0.63 |
| 6 | 0.11 |
| 7 | 0.18 |
| 8 | 0.19 |
| 9 | 1.12 |
| 11 | 1.10 |
| 16 | 0.16 |
| CI 976 | 1.04 |
| DUP 128 | 0.1 |

2) Hypocholesterolemic activity

Male rates (160–180 g) are subjected for 4 days to an Altromin C 1061 hypercholesterolemic diet, and concomitantly treated orally with compounds suspended in a 2% solution of Tween 80 in distilled water.

On day 5, the animals, which have not fasted, are anesthethized with ethyl ether and exsanguinated by drawing blood at the abdominal aorta onto EDTA. The blood is immediately centrifuged and the plasma stored at 4° C.

Plasma cholesterol is then assayed by the CHOD-PAP method (Boehringer-Mannheim Ref. 237574). The median effective dose ($ED_{50}$) corresponds to the dose which reduces the plasma cholesterol concentration by half relative to control animals.

| Compounds No. | $ED_{50}$ (mg/kg) |
|---|---|
| 2 | >10 |
| 3 | 4 |
| 4 | 0.5 |
| 5 | 1 |
| 6 | 1 |
| 7 | 0.2 |
| 8 | 10 |
| 14 | 1 |
| 16 | 0.15 |
| CI 976 | 8.3 |
| DUP 128 | 1.1 |

3) Antioxidant activity a) Chemical peroxidation.

In the presence of $Fe^{3+}$ and ADP, dihydroxyfumaric acid undergoes an autoxidation which generates oxygen free radicals. The latter bring about the peroxidation of hepatic microsomal lipids.

This peroxidation, performed on rat liver microsomes, is measured according to the thiobarbituric acid technique (formation of TBARS), as described by S. Y. H. Tse et al. (Biochemical Pharmacology, Vol. 42, No. 3, 459–464, 1991).

| Compounds No. | $IC_{50}$ (μM) |
|---|---|
| 2 | 5 |
| 3 | >10 |
| 4 | 0.5 |
| 5 | 5 |
| 6 | 0.3 |
| 7 | 0.6 |
| 8 | 3 |
| CI 976 | >10 |
| DUP 128 | >10 |
| Vitamin E | 2.3 | b) Oxidation of LDL.

Human LDL (Sigma L 2139) are oxidized with 10 μM $CuSO_4$. After an incubation period of 6 hours, the peroxidation is evaluated by measuring the TBARS by spectrophotometry at 532 nanometers.

| Compounds No. | IC$_{50}$ ($\mu$M) |
| --- | --- |
| 4 | 10 |
| 7 | 13 |
| 12 | 3 |
| 16 | 4 |
| CI 976 | 100 |
| DUP 128 | 30 |
| Vitamin E | 10 |

The compounds of the invention are hypocholesterolemic agents that inhibit ACAT and antioxidants, which can be used for the treatment of diseases such as hypercholesterolemia and atherosclerosis.

The pharmaceutical compositions can be presented in the form appropriate for oral, parenteral or local administration, for example in the form of capsules, including hard gelatin capsules, tablets, granules, liquid solutions, syrups or suspensions to be swallowed, and can contain the appropriate excipients.

The daily dosage can range from 10 to 3000 mg.

We claim:

1. An anilide derivative, selected from those of general formula I

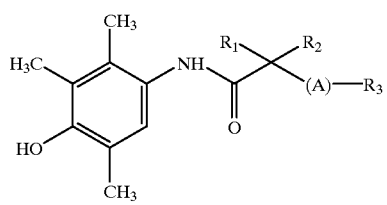

in which:

R$_1$ and R$_2$, which are identical or different, represent, independently of one another:
hydrogen
linear or branched C$_1$–C$_6$ alkyl
an aromatic group, selected from the group consisting of phenyl, naphthyl, and pyridyl, optionally substituted by one or more C$_1$–C$_4$ alkyl, C$_1$–C$_4$ alkoxy, hydroxyl, or halo;

R3 represents linear or branched C$_6$–C$_{15}$ alkyl or phenyl optionally substituted by one or more C$_1$–C$_4$ alkyl, C$_1$–C$_4$ alkoxy, hydroxyl or halo;

A represents oxygen or sulfur or sulfoxy;
and its various stereoisomers or enantiomers, and their mixtures, for the a compound exhibiting one or more asymmetric centers.

2. A compound according to claim 1, selected from the following:
2',3',5'-trimethyl-4'-hydroxy-α-(dodecylthio)propionanilide,
2',3',5'-trimethyl-4'-hydroxy-α-(dodecylthio)acetanilide,
2',3',5'-trimethyl-4'-hydroxy-α-(dodecylthio)butyranilide,
2',3',5'-trimethyl-4'-hydroxy-α-(dodecylthio)hexananilide,
2',3',5'-trimethyl-4'-hydroxy-α-(dodecylthio) isovaleranilide,
2',3',5'-trimethyl-4'-hydroxy-α-(dodecylthio)valeranilide,
2',3',5'-trimethyl-4'-hydroxy-α-dodecylthio-α-phenylacetanilide,
2',3',5'-trimethyl-4'-hydroxy-α-(dodecylthio) isobutyranilide,
2',3',5'-trimethyl-4'-hydroxy-α-(p-chlorophenylthio) isobutyranilide,
2',3',5'-trimethyl-4'-hydroxy-α-(p-chlorophenylsulfinyl) isobutyranilide,
2',3',5'-trimethyl-4'-hydroxy-α-(p-chlorophenoxy) isobutyranilide,
2',3',5'-trimethyl-4'-hydroxy-α-(dodecylsulfinyl) bobutyranilide,
2',3',5-trimethyl-4'-hydroxy-α-dodecylthio-α-(3,5-di-tert-butyl-4-hydroxy)phenylacetanilide,
2',3',5'-trimethyl-4'-hydroxy-α-dodecylthio-α-(p-methoxyphenyl)acetanilide,
2',3',5'-trimethyl-4'-hydroxy-α-dodecylthio-α-naphthylacetanilide, and
(+)-2',3',5'-trimethyl-4'-hydroxy-α-dodecylthio-α-phenylacetanilide.

3. Process for the preparation of a compound according to claim 1, wherein:

a) in a first stage, 2,3,6-trimethyl-4-aminophenol hydrochloride is treated with an α-haloacyl halide in the presence of a base, in order to provide the intermediate III

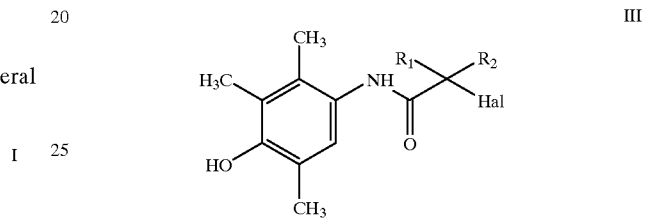

in which R$_1$ and R$_2$ are as defined in claim 1 and Hal represents a chlorine or bromine atom;

b) in a second stage, the intermediate III is treated with a derivative R$_3$(A)H, in which R$_3$ and A are as defined in claim 1, in a sodium/methanol or potassium tert-butoxide/tert-butanol medium.

4. Process for the preparation of a compound according to claim 3, wherein the intermediate III is alternatively obtained by reaction of an α-halo acid with 2,3,6-trimethyl-4-aminophenol hydrochloride in the presence of an activator, and of a base.

5. Process for the preparation of a compound according to claim 1, characterized in that 2,3,6-trimethyl-4-aminophenol hydrochloride is reached with a derivative VI

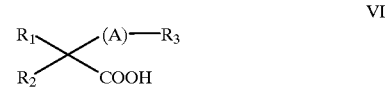

in which R$_1$, R$_2$, R$_3$ and A are as defined in claim 1, activation being carried out with ethyl chloroformate or with dicyclohexylcarbodiimide or 2-chloro-1-methylpyridinium iodide in the presence of a base.

6. A pharmaceutical composition comprising in addition to a pharmaceutically-acceptable vehicle, at least one compound of claim 1.

7. A pharmaceutical composition comprising, in addition to a pharmaceutically-acceptable vehicle, at least one compound of claim 2.

8. A method for treatment of hypercholesterolemia or atherosclerosis comprising the step of administering, to a living body suffering from the same, an effective amount of a compound of claim 1.

9. A method for treatment of hypercholesterolemia or atherosclerosis comprising the step of administering, to a living body suffering from the same, an effective amount of a compound of claim 2.

10. A process of claim 3 wherein the base is triethylamine.

11. A process of claim 4 wherein the activator is dicyclohexylcarbodiimide or 2-chloro-1-methylpyridinium iodide and the base is triethylamine.

12. A process of claim 5 wherein the base is triethylamine.

* * * * *

UNITED STATES PATENT AND TRADEMARK OFFICE
CERTIFICATE OF CORRECTION

PATENT NO. : 5,990,173
DATED : Nov. 23, 1999
INVENTOR(S) : J.F. Patoiseau; J.M. Autin; A.Delhon; P. Oms, D.Junquero It is certified that error appears in the above-indentified patent and that said Letters Patent is hereby corrected as shown below:

Column 15, line 49: Delete the word "the".

Column 16, line 54: Insert a -- , -- (comma) after the word "comprising".

Signed and Sealed this

Fourth Day of July, 2000

Attest:

Q. TODD DICKINSON

*Attesting Officer*  *Director of Patents and Trademarks*